US012558124B2

(12) United States Patent
    Zhao et al.

(10) Patent No.: US 12,558,124 B2
(45) Date of Patent: Feb. 24, 2026

(54) SYSTEM FOR ASSISTING IN IMPLANTING ELECTRODE WIRE AND METHOD FOR GUIDING ELECTRODE WIRE

(71) Applicant: SHANGHAI STAIRMED TECHNOLOGY CO., LTD., Shanghai (CN)

(72) Inventors: Zhengtuo Zhao, Shanghai (CN); Xue Li, Shanghai (CN); Yu Bao, Shanghai (CN)

(73) Assignee: SHANGHAI STAIRMED TECHNOLOGY CO., LTD., Shanghai (CN)

( * ) Notice: Subject to any disclaimer, the term of this patent is extended or adjusted under 35 U.S.C. 154(b) by 0 days.

(21) Appl. No.: 18/877,017

(22) PCT Filed: Jun. 29, 2022

(86) PCT No.: PCT/CN2022/102192
    § 371 (c)(1),
    (2) Date: Dec. 19, 2024

(87) PCT Pub. No.: WO2023/245702
    PCT Pub. Date: Dec. 28, 2023

(65) Prior Publication Data
    US 2025/0318853 A1      Oct. 16, 2025

(30) Foreign Application Priority Data
    Jun. 20, 2022    (CN) .......................... 202210717912.5

(51) Int. Cl.
    *A61B 17/34*       (2006.01)
    *A61B 34/20*       (2016.01)
    *A61F 2/72*        (2006.01)

(52) U.S. Cl.
    CPC ...... *A61B 17/3468* (2013.01); *A61B 17/3403* (2013.01); *A61B 34/20* (2016.02);
    (Continued)

(58) Field of Classification Search
    CPC . A61B 17/3468; A61B 17/3403; A61B 34/20; A61B 2034/2057; A61B 90/37; A61B 2090/371
    See application file for complete search history.

(56) References Cited

U.S. PATENT DOCUMENTS

| | | | |
|---|---|---|---|
| 2012/0046531 | A1 | 2/2012 | Hua |
| 2016/0100895 | A1 | 4/2016 | Piferi et al. |

(Continued)

FOREIGN PATENT DOCUMENTS

| | | |
|---|---|---|
| CN | 204618325 U | 9/2015 |
| CN | 108903916 A | 11/2018 |

(Continued)

OTHER PUBLICATIONS

Chinese Search Report in Chinese Application No. 202210717912.5 dated Jun. 21, 2024.

*Primary Examiner* — Katherine M Shi
*Assistant Examiner* — Mohammed S Adam
(74) *Attorney, Agent, or Firm* — Dilworth & Barrese, LLP.; Michael J. Musella, Esq.

(57) ABSTRACT

The present disclosure relates to a system for assisting in implanting an electrode wire, comprising: an electrode wire fixing apparatus; a guide needle fixing apparatus; a movement mechanism; a first camera, arranged on a first side of a plane and towards a metal part, the first camera having a first optical path; a second camera, arranged on the first side of the plane and towards the metal part, the second camera having a second optical path at an angle to the first optical path; and a processing apparatus, configured to identify a
(Continued)

relative position of the end of a guide needle to a through hole based on images shot by the first camera and the second camera, and control the movement mechanism to drive the electrode wire fixing apparatus and/or the guide needle fixing apparatus to move, so that the end of the guide needle is aligned with the through hole. The present disclosure further relates to a method for guiding an electrode wire.

19 Claims, 8 Drawing Sheets

(52) U.S. Cl.
CPC .................. *A61B 2017/3409* (2013.01); *A61B 2034/2057* (2016.02); *A61F 2/72* (2013.01)

(56) References Cited

U.S. PATENT DOCUMENTS

| | | |
|---|---|---|
| 2017/0245772 A1 | 8/2017 | Bierbrauer et al. |
| 2020/0108246 A1 | 4/2020 | Cadwell |

FOREIGN PATENT DOCUMENTS

| | | |
|---|---|---|
| CN | 109200470 A | 1/2019 |
| CN | 209252829 U | 8/2019 |
| CN | 110841186 A | 2/2020 |
| CN | 112370064 A | 2/2021 |
| CN | 112999511 A | 6/2021 |
| CN | 113041496 A | 6/2021 |
| CN | 114376580 A | 4/2022 |
| CN | 114631822 A | 6/2022 |
| EP | 2767306 A2 | 8/2014 |
| JP | 2017217457 A | 12/2017 |

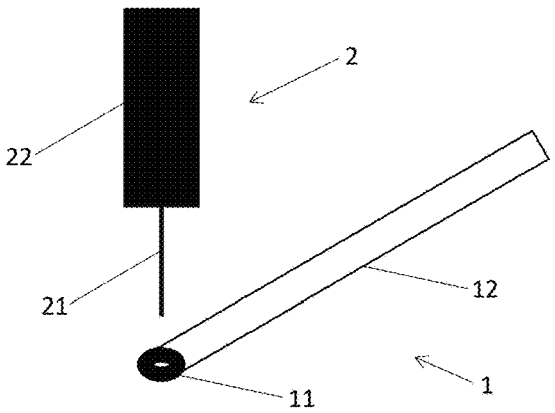
Fig. 3A
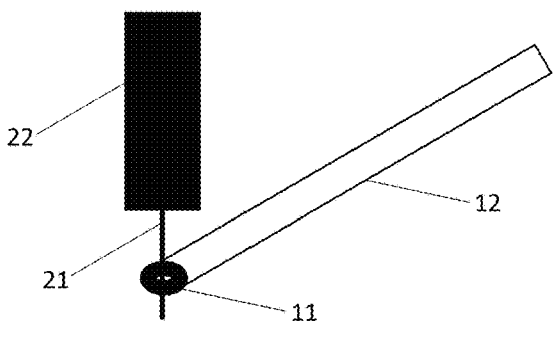
Fig. 3B
Fig. 4A

SYSTEM FOR ASSISTING IN IMPLANTING ELECTRODE WIRE AND METHOD FOR GUIDING ELECTRODE WIRE

TECHNICAL FIELD

The present disclosure relates to a system for assisting in implanting an electrode wire and a method for guiding an electrode wire.

BACKGROUND

Invasive brain-computer interface is to implant electrodes that can measure and release electrical signals into the brain, and decode neural signals through the detected electrical signals; it can also release signals through implanted electrodes to regulate the brain and then regulate the life activities of the whole organism. The decoding of electrical signals collected by electrodes can be applied to prosthetic control to help disabled people recover their limb functions; the release of electrical signals of electrodes can be applied to the regulation of neurological diseases such as epilepsy.

In the application of invasive brain-computer interface, electrode implantation is a very difficult problem. In order to reduce the rejection of electrodes in vivo and reduce implantation damage, flexible electrodes have been developed. However, flexible electrodes are more difficult to implant because of their "flexibility" characteristics.

In order to reduce damage to the tissue of the implanted target, the width and thickness of the flexible electrode are often configured to have very small dimensions, for example, the width and thickness of the nanoscale or micron scale; at the same time, in order to facilitate the establishment of an electrical connection between the implanted target and the electrical circuit, the electrode wire may have a length that is several orders of magnitude greater than its width and thickness, for example a length on the order of centimeters. Accordingly, the flexible electrode according to the present disclosure may be configured as a strip or a filament. Therefore, the flexible electrode according to the present disclosure is also referred to as an electrode wire.

SUMMARY

One of the objects of the present disclosure is to provide a system for assisting in implanting an electrode wire and a method for guiding an electrode wire.

According to a first aspect of the present disclosure, there is provided a system for assisting in implanting an electrode wire, comprising: an electrode wire fixing means for fixing an electrode wire, the electrode wire being provided at an end thereof with a substantially planar metal portion having a through hole formed therein, the metal portion being at least partially suspended from the electrode wire fixing means; a guide needle fixing means for fixing a metal guide needle, the guide needle having an end configured to mate with the through hole; a movement mechanism configured to drive the guide needle fixing means to move such that the guide needle is moved from a first side of a plane on which the metal portion is located to a second side of the plane so as to be engaged with the metal portion, and to drive the electrode wire fixing means and/or the guide needle fixing means to move substantially parallel to the plane; a first camera arranged on a first side of the plane and facing the metal portion, the first camera having a first optical path; a second camera arranged on a first side of the plane and facing the metal portion, the second camera having a second optical path at an angle to the first optical path; and a processing means configured to recognize a relative position between the end of the guide needle and the through hole based on images captured by the first camera and the second camera, and control the movement mechanism to drive the electrode wire fixing means and/or the guide needle fixing means to move such that the end of the guide needle is aligned with the through hole.

According to a second aspect of the present disclosure, there is provided a method for guiding an electrode wire, comprising performing the following operations in an environment where a predetermined brightness is reached: viewing, by two cameras, from different angles, an engagement portion of the electrode wire for engaging a guide needle and an end of the guide needle, wherein the engagement portion of the electrode wire is provided with a through hole through which the end of the guide needle can penetrate and the electrode wire is arranged so that at least a portion of the engagement portion near the through hole is suspended, wherein both the engagement portion of the electrode wire and the end of the guide needle are configured to have a light transmittance of less than 50%; and recognizing, by a processing means, a relative position between the end of the guide needle and the through hole based on the images acquired from the two cameras and controlling the movement of the electrode wire and/or the guide needle so that the end of the guide needle is aligned with the through hole, wherein the predetermined brightness in the environment is provided by: a light source dedicated to the environment; and/or a lighting equipment in the room in which the environment is located.

Other features and advantages of the present disclosure will become apparent from the following detailed description of exemplary embodiments of the present disclosure with reference to the accompanying drawings.

BRIEF DESCRIPTION OF DRAWINGS

The accompanying drawings, which form a part of the specification, describe embodiments of the present disclosure and, together with the specification, serve to explain the principles of the present disclosure.

FIGS. 3A and 3B are schematic views of a guide needle being engaged with an electrode wire in an embodiment of the present disclosure.

FIGS. 4A to 4C are schematic diagrams illustrating an arrangement of a guide needle and an electrode wire in an embodiment of the present disclosure.

Figure 1:
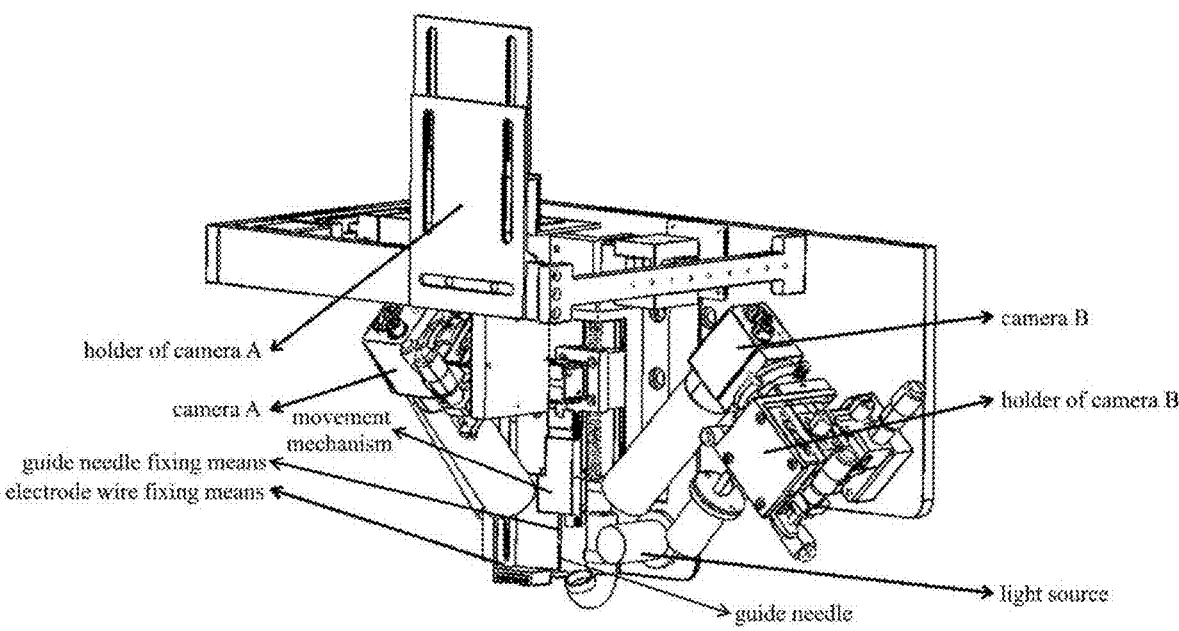
FIG. 1 is a schematic diagram of a system for assisting in implanting an electrode wire according to an embodiment of the present disclosure.

Note that, in the embodiments described below, the same parts or parts having the same functions may be denoted by the same reference numerals in different drawings, and redundant description thereof may be omitted. In some cases, similar reference numerals and letters are used to represent similar items, and therefore, once an item is defined in one figure, it does not need to be further discussed in subsequent figures.

For case of understanding, the positions, dimensions, ranges, and the like of each configuration illustrated in the drawings and the like may not indicate the actual positions, dimensions, ranges, and the like. Therefore, the present disclosure is not limited to the positions, dimensions, ranges, and the like disclosed in the drawings and the like.

DETAILED DESCRIPTION

The present disclosure will be described below with reference to the accompanying drawings, in which several embodiments of the present disclosure are illustrated. It should be understood, however, that the present disclosure may be presented in many different ways and is not limited to the embodiments described below; in fact, the embodiments described below are intended to complete the disclosure of the present disclosure and fully illustrate the scope of protection of the present disclosure to those skilled in the art. It should also be understood that the embodiments disclosed herein can be combined in various ways to provide more additional embodiments.

It should be understood that the terms used herein are used to describe specific embodiments only and are not intended to limit the scope of the present disclosure. All terms (including technical and scientific terms) used herein have the meanings commonly understood by those skilled in the art unless otherwise defined. For the sake of conciseness and/or clarity, well-known functions or structures may not be described in detail.

Herein, when an element is said to be "on" another element, "attached" to another element, "connected" to another element, "coupled" to another element, or "contacting" another element, or the like, the element may be directly on, attached to, connected to, coupled to, or contacting the other element, or intermediate elements may be present. In contrast, when an element is said to be "directly" "on" another element, "directly attached" to another element, "directly connected" to another element, "directly coupled" to another element, or "directly contacting" another element, there will be no intermediate elements. Herein, one feature is arranged "adjacent" to another feature, which may mean that one feature has a portion that overlaps an adjacent feature or a portion that is located above or below an adjacent feature.

Herein, reference may be made to elements or nodes or features that are "coupled" together. Unless explicitly stated otherwise, "coupled" means that one element/node/feature may be mechanically, electrically, logically, or otherwise coupled to another element/node/feature in a direct or indirect manner to allow interaction, even if the two features may not be directly connected. That is, "coupled" is intended to include direct and indirect joining of elements or other features, including joining with one or more intermediate elements.

Herein, spatial relationship terms such as "above", "below", "left", "right", "front", "rear", "high", "low" etc. may illustrate the relationship of one feature to another feature in the drawings. It should be understood that the spatial relationship terms encompass different orientations of the means in use or operation in addition to the orientations shown in the figures. For example, when the means in the drawings is inverted, a feature that was previously described as being "below" other features may be described as being "above" other features. The means may also be oriented in other ways (rotated 90 degrees or in other orientations), where the relative spatial relationships will be interpreted accordingly.

Herein, the term "A or B" includes "A and B" and "A or B" and does not exclusively include only "A" or only "B" unless specifically stated otherwise.

Herein, the term "exemplary" means "used as an example, instance, or illustration" rather than as a "model" to be precisely replicated. Any implementation exemplarily described herein is not necessarily to be construed as preferred or advantageous over other implementations. Moreover, the present disclosure is not limited by any stated or implied theory set forth in the above-described technical field, background, summary, or detailed description.

Herein, the term "substantially" is meant to include any minor variation caused by defects in design or manufacture, tolerances of means or elements, environmental influences, and/or other factors. The term "substantially" also allows for differences from perfect or ideal situations due to parasitic effects, noise, and other practical considerations that may exist in actual implementations.

In addition, similar terms such as "first" and "second" may also be used herein for reference purposes only, and are therefore not intended to be limiting. For example, the words "first", "second" and other such numerical words referring to structures or elements do not imply order or sequence unless the context clearly dictates otherwise.

It should also be understood that the word "comprising/including", when used herein, indicates the presence of the indicated features, steps, operations, units, and/or components, but does not preclude the presence or addition of one or more other features, steps, operations, units, and/or components, and/or combinations thereof.

Figure 2A:
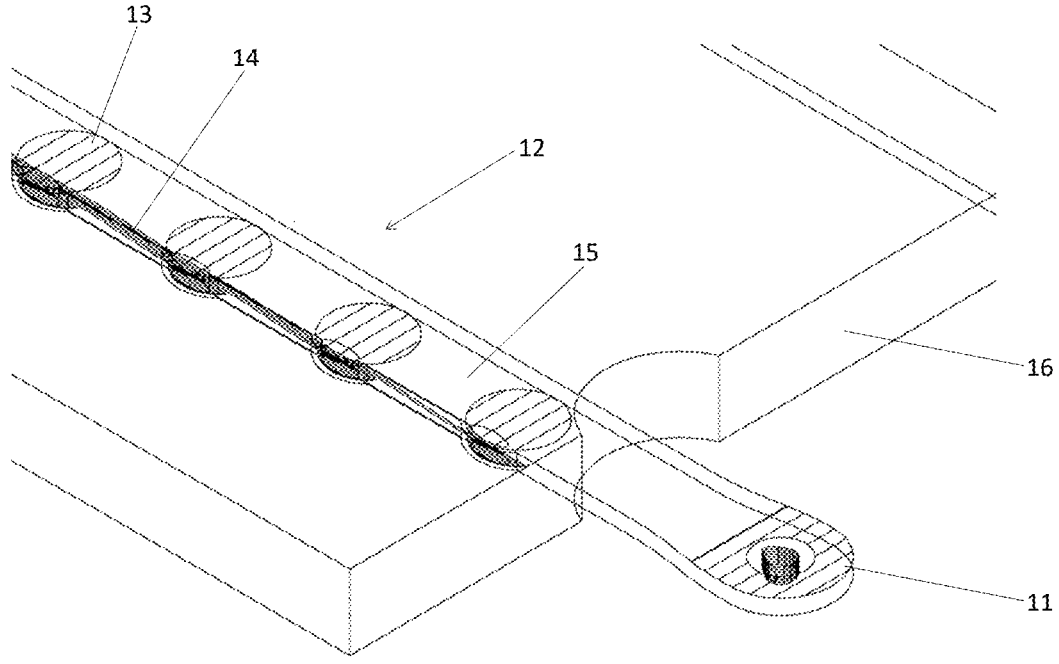
FIG. 2A is a schematic perspective view of an electrode wire suitable for use in an embodiment of the present disclosure.
Figure 2B:
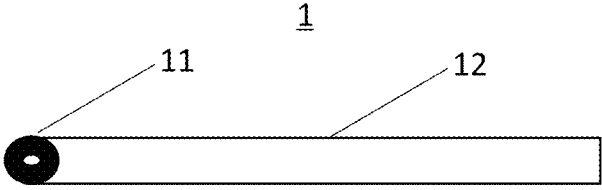
FIG. 2B is a highly simplified schematic plan view of an electrode wire suitable for use in an embodiment of the present disclosure.

Embodiments of the present disclosure provide a system for assisting in implanting an electrode wire and a method for guiding an electrode wire. FIG. 2A is a perspective schematic view of an electrode wire suitable for use in an embodiment of the present disclosure, and FIG. 2B is a highly simplified schematic plan view of an electrode wire suitable for use in an embodiment of the present disclosure. The electrode wire 1 includes a front end that can be implanted into a target, such as biological tissue, and a rear end (not shown) for connecting an electrical circuit. The insulating layer 15 extends between its front and rear ends to mainly provide mechanical strength of the electrode wire 1. The electrode wire 1 includes, at its front end, an engagement portion 11 for engaging the guide needle 2. In the illustrated example, a through hole through which the end of the guide needle 2 can be inserted is opened in the engagement portion 11 so that the electrode wire 1 is engaged with the guide needle 2. The front end of the electrode wire 1 may collect an electrical signal from a target, for example, through each electrode site 13, and transmit the collected electrical signal to the electrical circuit connected to the rear end of the electrode wire 1 through a lead 14 in the electrode wire 1. Furthermore, the rear end of the electrode wire 1 may receive electrical signals from the electrical circuit to which it is connected and apply the received electrical signals to the implanted target through the lead 14 and the electrode sites 13 in the electrode wire 1. It should be noted that, for the sake of simplicity, only the section 12 of the electrode wire 1 close to the engagement portion 11 is shown in FIGS. 2A and 2B. In order to protect the electrode wire 1 and facilitate use, the electrode wire 1 may be adhered to the substrate 16 when manufactured. In some embodiments, the substrate 16 may comprise a polymer film.

FIGS. 3A and 3B are schematic views of the guide needle 2 being engaged with the electrode wire 1 in an embodiment of the present disclosure. The guide needle 2 has an end configured to mate with (for example, be able to penetrate) a through hole in the engagement portion 11. In the example shown in FIGS. 3A and 3B, the guide needle 2 includes a first portion 21 having an outer diameter smaller than the inner diameter of the through hole of the engagement portion 11 and a second portion 22 having an outer diameter larger than the inner diameter of the through hole of the engagement portion 11. For simplicity, the second portion 22 of the guide needle 2 shown in FIGS. 3A and 3B may be only partial, i.e. only the section of the second portion 22 close to the first portion 21 may be shown, and in practical implementation, the second portion 22 may also comprise a longer section extending upwardly. FIGS. 3A and 3B show an example of engagement of the guide needle 2 and the electrode wire 1. Since the first portion 21 is smaller than the inner diameter of the engagement portion 11 and the second portion 22 is larger than the inner diameter of the engagement portion 11, as shown in FIG. 3B, the first portion 21 of the guide needle 2 can pass through the through hole of the engagement portion 11 and the second portion 22 cannot pass through the through hole of the engagement portion 11. After the first portion 21 has passed through the engagement portion 11, the guide needle 2 continues to move downward (in the direction shown in the figure), so that the engagement portion 11 of the electrode wire 1 is stopped between the first portion 21 and the second portion 22, so that the guide needle 2 can be engaged with the electrode wire 1 through the engagement portion 11. After the guide needle 2 is engaged with the electrode wire 1, the guide needle 2 can guide the position of the electrode wire 1, that is, the electrode wire 1 can be guided from the first position to the second position. For example, in the direction shown in the figure, the guidance is performed in an up-down direction, a left-right direction, and/or a direction perpendicular to the paper surface. In one example, the guide needle 2 guides the electrode wire 1 to implant the electrode wire 1 into a target. After engagement of the guide needle 2 with the electrode wire 1, the guide needle may continue to move downward (in the direction shown in the figure) until at least a portion of the first portion 21 and the second portion 22 of the guide needle 2 enters the target, thereby implanting the engagement portion 11 of the electrode wire 1 and at least a portion of the section 12 adjacent to the engagement portion 11 into the target.

In the above-described process, it is necessary to make the first portion 21 of the guide needle 2 pass through the through hole of the engagement portion 11. Since the size of the electrode wire 1 is extremely small, the width thereof is often configured to have a size, for example, on the nanometer or micrometer scale, as described above, it is difficult to make the first portion 21 of the guide needle 2 pass through the through hole of the engagement portion 11.

FIG. 1 is a schematic diagram of a system for assisting in implanting an electrode wire according to an embodiment of the present disclosure. The system includes an electrode wire fixing means for fixing an electrode wire, a guide needle fixing means for fixing a guide needle, a movement mechanism for driving the movement of the electrode wire fixing means and/or the guide needle fixing means, a camera A and a camera B for observing engagement of the guide needle and the electrode wire, and a processing means (not shown) for controlling the movement mechanism.

Figure 4B:
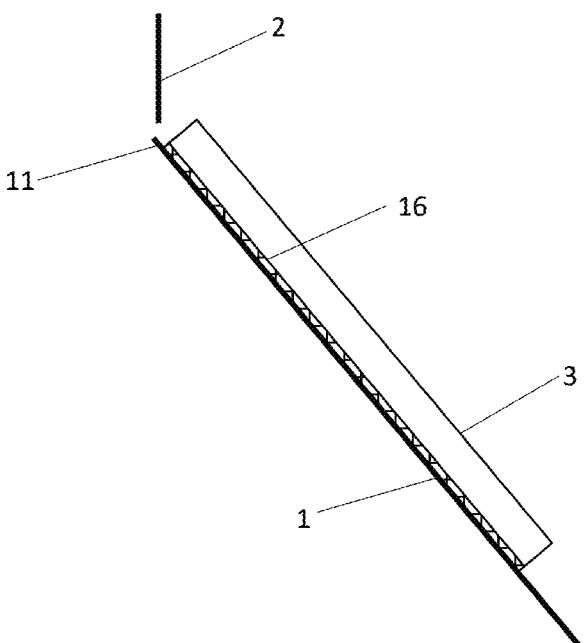
Figure 4C:
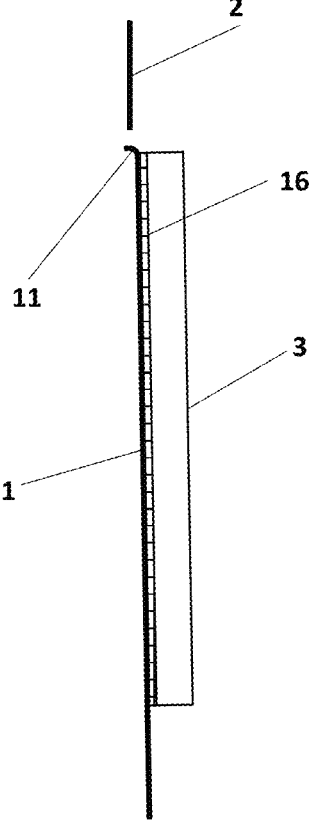

FIGS. 4A to 4C show the arrangement of the electrode wire 1 on the electrode wire fixing means 3. The electrode wire fixing means 3 may be configured as a support plate. As described above, the electrode wire 1 may be adhered to a substrate 16, and thus the electrode wire 1 may be fixed to the electrode wire fixing means 3 via the substrate 16. For example, as shown in FIG. 2A, the electrode wire 1 may be adhered to a first surface of the substrate 16, and a second surface of the substrate 16 opposite the first surface may be adhered to the electrode wire fixing means 3, as shown in FIGS. 4A to 4C. In order to facilitate the engagement of the guide needle 2 and the electrode wire 1, the engagement portion 11 of the electrode wire 1 needs to be arranged so that at least a portion near the through hole is suspended, that is, the upper and lower portions thereof are not blocked, for example, by the substrate 16, the electrode wire fixing means 3, or the like. Here, "upper" and "lower" refer to opposite sides of the plane on which the engagement portion 11 extends, and are above and below the plane on which the engagement portion 11 extends from the viewing angle shown in FIG. 2A. For example, in the example of FIG. 2A, the engagement portion 11 is suspended from the substrate 16. In the example of FIGS. 4A to 4C, the engagement portion 11 is suspended from the substrate 16 and the electrode wire fixing means 3. After aligning the through hole in the engagement portion 11, the guide needle fixing means 23, driven by the movement mechanism, can be moved downward, thereby driving the guide needle 2 to move downward and causing the first portion 21 to pass through the through hole so that the guide needle 2 is engaged with the electrode wire 1.

Figure 5A:
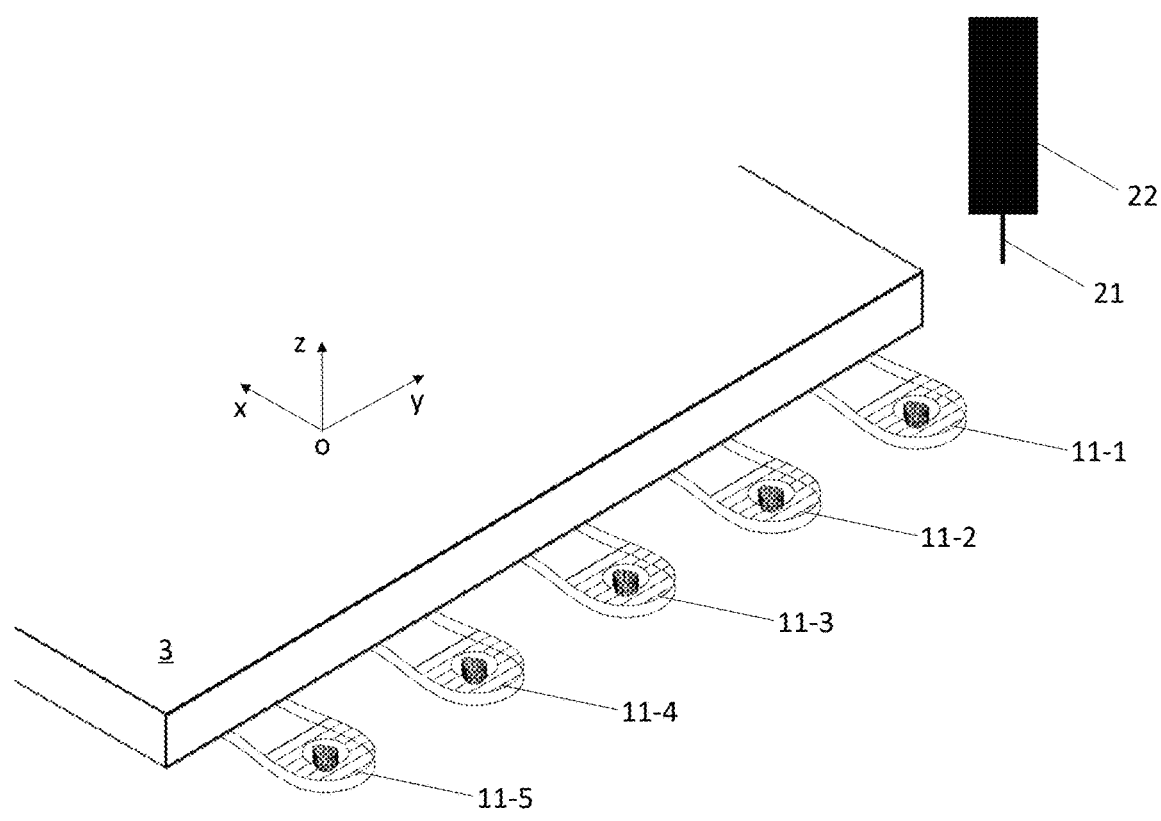
FIGS. 5A and 5B are schematic diagrams illustrating an arrangement of a guide needle and an electrode wire in an embodiment of the present disclosure.

In practical implementations, the electrode wires 1 are generally manufactured in batches. A plurality of electrode wires 1 manufactured in batch may be adhered side by side to a substrate 16, and the substrate 16 may be fixed to the electrode wire fixing means 3, so that the plurality of electrode wires 1 are fixed side by side to the electrode wire fixing means 3, as shown in FIG. 5A. In this case, the plurality of electrode wires may be arranged side by side so that the through holes in the engagement portions 11-1 to 11-5 of the respective electrode wires are substantially aligned. The first portion 21 (also referred to as the end 21) of the guide needle 2 may be sequentially aligned with the through holes in the engagement portions 11-1 to 11-5 of the respective electrode wires 1 in order to be sequentially engaged with the respective electrode wires 1, as shown in the perspective view 5A and the plan view 5B, respectively.

In the system for assisting in implanting an electrode wire according to an embodiment of the present disclosure, the engagement portion 11 of the electrode wire 1 for engaging the guide needle 2 and the end 21 of the guide needle 2 are viewed from different angles by two cameras, such as the camera A and the camera B, respectively, and images within the respective visual fields are captured. The relative position between the end 21 of the guide needle 2 and the through hole in the engagement portion 11 is recognized by the processing means based on the images acquired from the two cameras, and the movement mechanism drives the electrode wire fixing means and/or the guide needle fixing means to move so as to bring the electrode wire 1 and/or the guide needle 2 into motion so that the end 21 of the guide needle 2 is aligned with the through hole in the engagement portion 11. It should be understood that the term "image" in the present disclosure includes pictures and videos.

In order for the engagement portion 11 of the electrode wire 1 and the end 21 of the guide needle 2 to be clearly observed in the camera, it is necessary to satisfy two conditions: the environment reaches a predetermined brightness, and the light transmittance of both the engagement portion 11 of the electrode wire 1 and the end 21 of the guide needle 2 is small. Here, the "environment" refers to an environment in which the engagement portion 11 and the end 21 are observed. As described above, the engagement portion 11 is disposed in a suspended manner, so that there is only air in a certain range around the engagement portion 11, and there is no other barrier. Before the end 21 of the guide needle 2 passes through the through hole of the engagement portion 11, it is also suspended, that is, there is only air in a certain range around the end 21, and there is no other barrier. Therefore, in a case where the brightness is sufficient, the engagement portion 11 and the end 21 can be clearly observed in the camera as long as the light transmittance of the engagement portion 11 and the end 21 can be clearly distinguished from that of air.

In some embodiments, both the engagement portion 11 of the electrode wire 1 and the end 21 of the guide needle 2 are configured to have a light transmittance of less than 50%. In a preferred embodiment, both the engagement portion 11 of the electrode wire 1 and the end 21 of the guide needle 2 comprise metal. For example, the engagement portion 11 may be configured as a substantially planar metal portion in which a through hole is provided. The guide needle 2 may be configured as a metal guide needle. Since metal has a small light transmittance, the engagement portion 11 and the end 21 formed of metal are used to facilitate clear observation in a camera. Further, since it is necessary to observe both the engagement portion 11 of the electrode wire 1 and the end 21 of the guide needle 2 at the same time in each camera, the difference in light transmittance of the two cannot be so large as to require different brightness and/or camera parameters in order to observe both clearly. Therefore, in some embodiments, the difference in light transmittance between the engagement portion 11 of the electrode wire 1 and the end 21 of the guide needle 2 is less than 15%.

A method of bringing the environment to a predetermined brightness may include setting the system at a position where the brightness satisfies the requirement, using a light source, and the like. Since systems and methods according to embodiments of the present disclosure may not be limited to a light source of a particular color/wavelength, a predetermined brightness in an environment may be provided by a light source dedicated to the environment in the system, or may also be provided by a pre-existing lighting means (e.g., an indoor lighting lamp) in a room in which the system is located. The system shown in FIG. 1 includes a light source dedicated to the environment in the system. The light source may be configured to provide visible light, provide infrared light, provide only white light, or provide both white light and blue light. The light source may be configured such that the light provided by the light source is irradiated after diffuse reflection onto the engagement portion 11 of the electrode wire 1, or it may be configured such that the light provided by the light source directly irradiates onto the engagement portion 11 of the electrode wire 1. In embodiments in which the light source is configured to provide both white light and blue light, the light source includes a first light source providing white light and a second light source providing blue light. The first light source may be a light source disposed coaxially with the lens of at least one of the two cameras (the lens of camera A or the lens of camera B), which may be integrated inside the lens, and when in use, there is a spot of white light irradiated by this light source when viewed by the lens. The second light source may be a ring-shaped light source sleeved outside the lens of at least one camera (the lens of camera A or the lens of camera B).

Figure 7A:
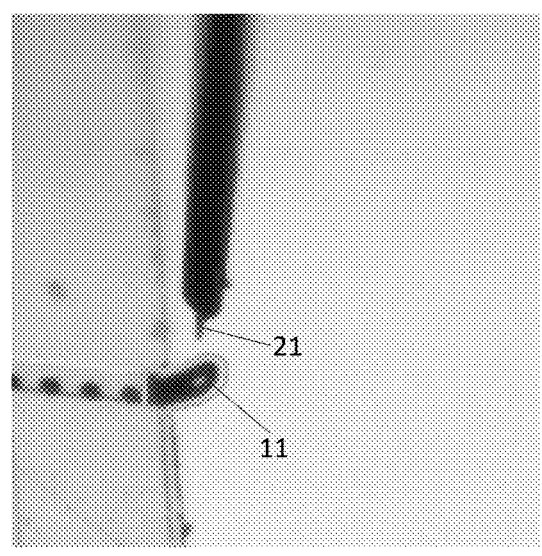
FIGS. 7A and 7B are schematic diagrams showing images captured by two cameras, respectively, in the system shown in FIG. 1.
Figure 7A:
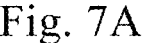
Figure 7B:
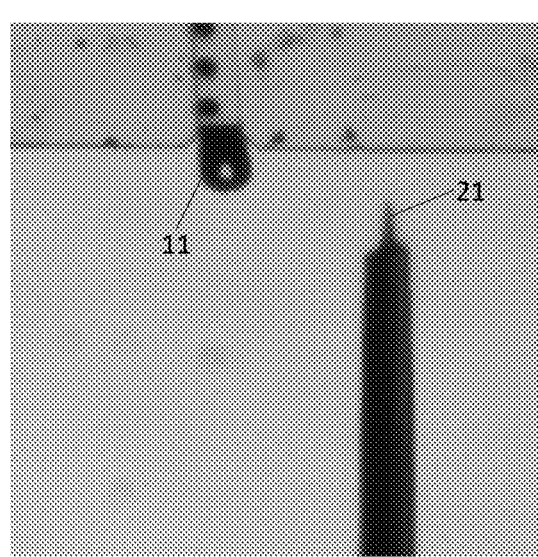

An example of an image in which the engagement portion 11 and the end 21 are observed by a camera is shown in FIGS. 7A and 7B. It can be seen that when both the environment brightness and the light transmittance of the object to be observed satisfy the requirements, the engagement portion 11 and the end 21 can be clearly observed in the camera. Furthermore, in order to make less interference in the image observed by the camera, it is preferable to use a camera having a smaller depth of field. In some embodiments, camera A and camera B are configured to have a depth of field of less than 1 millimeter. Since the object to be observed, that is, the engagement portion 11 of the electrode wire 1 and the end 21 of the guide needle 2 are both small in size, it is preferable to use a camera having a small field of view.

The movement mechanism in the system according to an embodiment of the present disclosure may drive the electrode wire fixing means 3 and/or the guide needle fixing means 23 to move. For convenience of description, in the present disclosure, as shown in FIG. 5A, a plane in which the engagement portion 11 substantially extends is defined as an xoy plane, and a direction perpendicular to the xoy plane is defined as a z-axis direction. Note that, when a plurality of electrode wires 1 are included, the planes on which the engagement portions 11-1 to 11-5 of each electrode wires 1 extend may not completely overlap (because of the flexibility characteristics of the electrode wires 1, manufacturing errors, and the like), and at this time, the xoy plane may be a plane on which the respective engagement portions 11-1 to 11-5 substantially extend together, for example, a plane on which the substrate 16 extends. The movement mechanism may drive the guide needle fixing means 23 to move such that the guide needle 2 is moved along the z-axis direction from a first side of the xoy plane (for example, at the viewing angle shown in FIG. 5A as the upper side) toward a second side of the xoy plane (for example, at the viewing angle shown in FIG. 5A as the lower side) so as to be engaged with the engagement portion 11. It should be noted that a segmented reference numeral, for example, the engagement portion 11-1, is used herein. When used in this way, it means that each of the engagement portions 11-1 to 11-5 can be distinguished. When it is not necessary to distinguish the respective engagement portions of the engagement portions 11-1 to 11-5, only the first half of the segmented reference numerals may be used to collectively refer to them, that is, these are collectively referred to as engagement portions 11.

Furthermore, the movement mechanism can also drive the electrode wire fixing means 3 and/or the guide needle fixing means 23 to move substantially parallel to the xoy plane, for example substantially parallel to the xoy plane in a first direction and a second direction perpendicular to each other. The movement mechanism drives either of the electrode wire fixing means 3 and the guide needle fixing means 23 to move, i.e. enabling a relative movement between the engagement portion 11 of the electrode wire 1 and the end 21 of the guide needle 2, so that the end 21 is aligned with the engagement portion 11. In the operation of aligning the end 21 with the engagement portion 11, only the relative movement between the end 21 and the engagement portion 11 along the xoy plane is required, that is, movement along the z-axis direction is not required, and thus a plurality of engagement portions 11-1 to 11-5 and the end 21 are shown in a plan view in FIG. 5B.

Figure 5B:
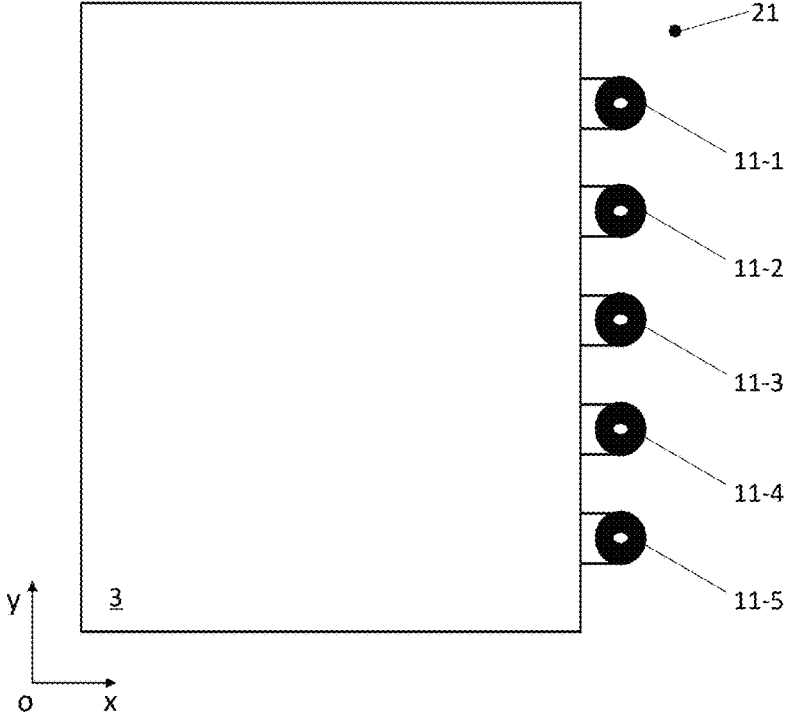
Figure 6A:
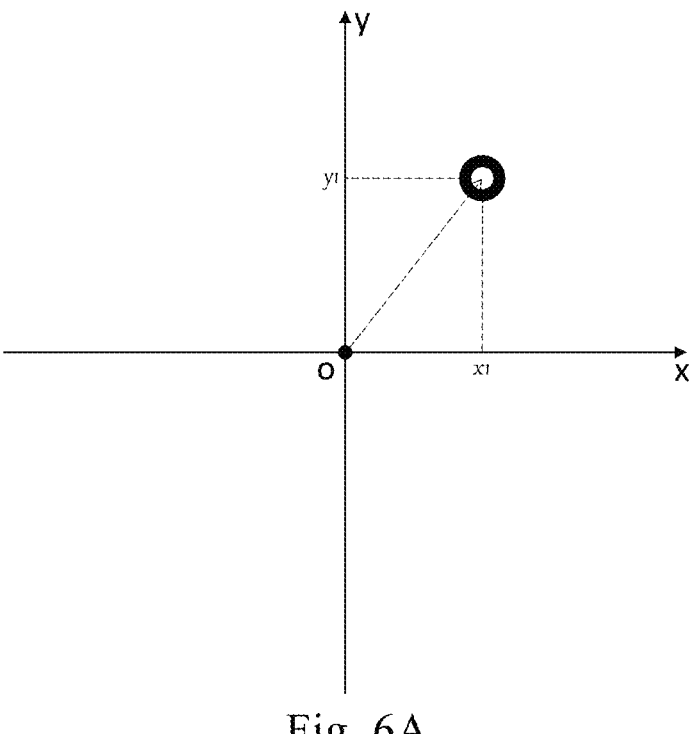
FIG. 6A is a schematic diagram of the planar displacement required for a guide needle to be aligned with a through hole in an embodiment of the present disclosure.

In the drawings of the present disclosure, for ease of description, the initial position of the relative movement is shown as a dot (corresponding to the end 21 in the plan view of FIG. 5B), and the target position of the relative movement is shown as a ring (corresponding to the engagement portion 11 in the plan view of FIG. 5B), referring to FIG. 6A. Therefore, in the description herein, it is described that controlling the movement of the guide needle fixing means 23 substantially parallel to the xoy plane and thereby drive the end 21 of the guide needle 2 to move. It will be understood by those skilled in the art that controlling the movement of the electrode wire fixing means 3 substantially parallel to the xoy plane and thereby driving the movement of the engagement portion 11 of the electrode wire can be done similarly. As shown in FIG. 6A, if it is necessary to control the movement of the end 21 along the xoy plane from the original dot o to the target position (x1, y1), it can be controlled to move a distance x1 along the x-axis direction and a distance y1 along the y-axis direction, respectively. It should be noted that although the x-axis direction shown in FIG. 5B is a direction in which the length of the electrode wires extends, and the y-axis direction is a direction in which a plurality of electrode wires are arranged side by side, those skilled in the art will understand that this is an assumption made for convenience of illustration only. In practical implementation, the x-axis direction and the y-axis direction only need to be two directions perpendicular to each other on the xoy plane, that is, the first direction and the second direction as described above in which the movement mechanism drives the electrode wire fixing means 3 and/or the guide needle fixing means 23 to move substantially parallel to the xoy plane.

Figure 6B:
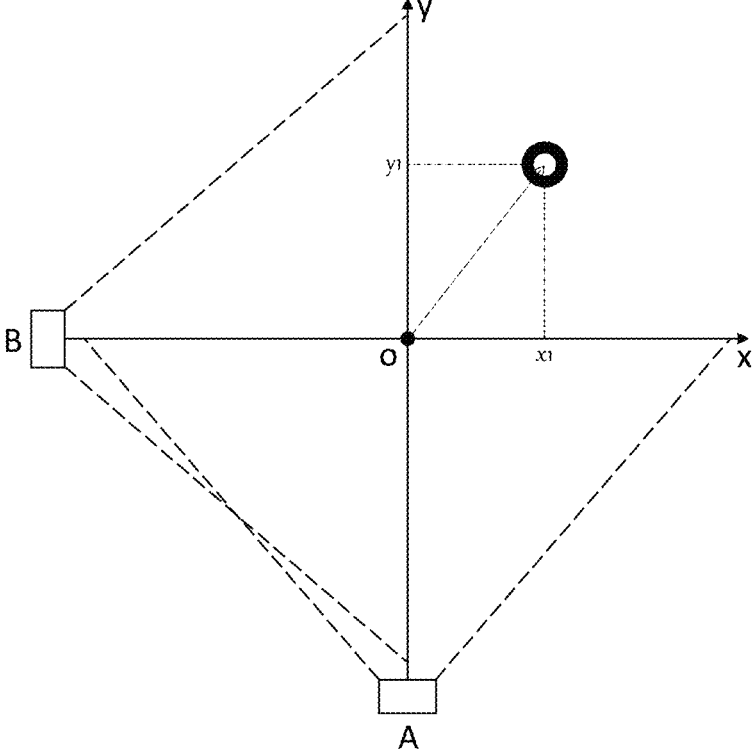
FIGS. 6B and 6C are schematic diagrams illustrating an arrangement of cameras in embodiments of the present disclosure.
Figure 6C:
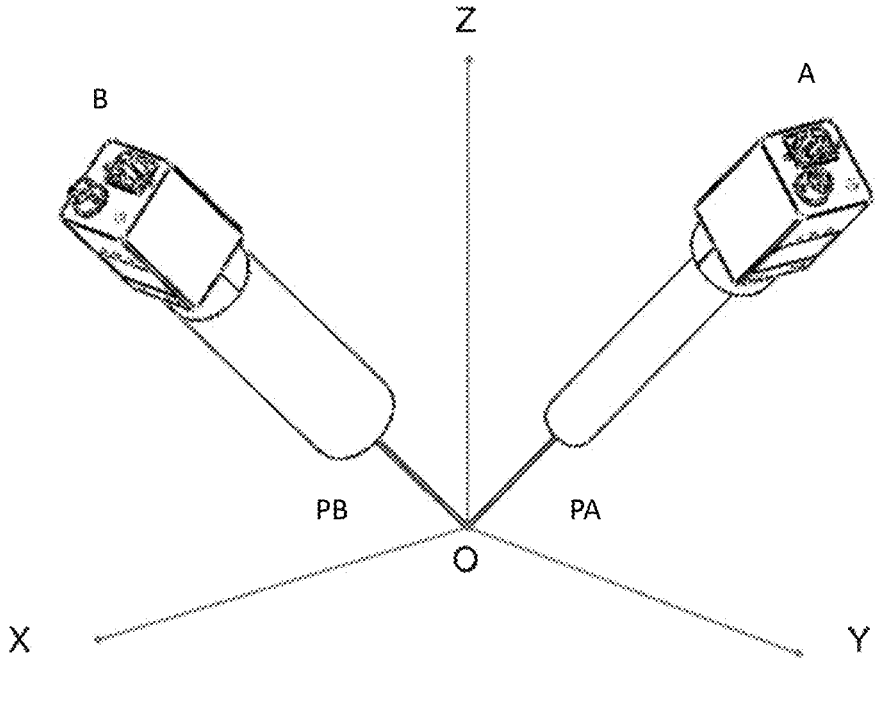

In some embodiments, as shown in FIGS. 6B and 6C, the camera A and the camera B may be arranged such that the respective optical paths, that is, the optical paths PA and PB, are perpendicular to each other, and the optical path PA of the camera A is perpendicular to the x-axis direction and the optical path PB of the camera B is perpendicular to the y-axis direction. The dashed line in the figure schematically represents the field of view of the respective camera. As can be seen, the cameras A and B are placed so that the camera A can directly observe the relative position along the x-axis between the through hole of the engagement portion 11 and the end 21, and the camera B can directly observe the relative position along the y-axis. Thus, the processing means only needs to compare the pixel position difference between the through hole of the engagement portion 11 and the end 21 of the guide needle 2 in the image A captured by the camera A, according to which the distance x1 at which the end 21 should move in the x-axis direction can be determined; accordingly, it is only necessary to compare the pixel position difference between the through hole of the engagement portion 11 and the end 21 of the guide needle 2 in the image B captured by the camera B, according to which the distance y1 at which the end 21 should move in the y-axis direction can be determined. Accordingly, the processing means can determine a control signal to the movement mechanism based on the determined distances x1 and y1, thereby controlling the movement mechanism to drive the guide needle fixing means 23 to carry the end 21 to move the distance x1 along the x-axis and the distance y1 along the y-axis so as to reach the target position, i.e. to align with the through hole of the engagement portion 11.

FIG. 6B shows arrangement positions of the camera A and the camera B from the viewing angle of a plan view, and FIG. 6C shows the arrangement positions from the viewing angle of a perspective view. As can be seen, the cameras A and B are not arranged on the xoy plane, but are both arranged on the first side of the xoy plane (i.e. the side where the end 21 is located before the end 21 is moved along the z-axis to pass through the through hole) and towards the engagement portion 11. The camera A faces the engagement portion 11 at a first angle to the xoy plane, and the camera B faces the engagement portion 11 at a second angle to the xoy plane. Those skilled in the art will appreciate that while the first angle and the second angle shown in the embodiment of FIG. 1 or FIG. 6C are substantially equal, in other embodiments, the first angle and the second angle may be different. In some embodiments, at least one of the first angle and the second angle is less than 90 degrees. Preferably, at least one of the first angle and the second angle is between 20 degrees and 80 degrees. In this way, both the through hole of the engagement portion 11 and the end 21 of the guide needle 2 can be viewed at the same time with relatively clear clarity, as shown in FIGS. 7A and 7B.

The processing of the images of the camera A and the camera B by the processing means comprises performing a black-and-white binarization processing on the image A captured by the camera A and the image B captured by the camera B, and performing a contour segmentation. The characteristic area in which the engagement portion 11 is located and the characteristic area in which the end 21 of the guide needle 2 is located are detected by the recognition algorithm. The pixel position difference between the through hole in the engagement portion 11 and the end 21 of the guide needle 2 in the images A, B is compared, and a control signal to the movement mechanism is determined according to the pixel position difference, thereby controlling the movement mechanism to drive the electrode wire fixing means 3 and/or the guide needle fixing means 23 to move. In response to the pixel position difference between the through hole in the engagement portion 11 and the end 21 of the guide needle 2 in the images A, B being less than a predetermined value, i.e. the end 21 is considered to be aligned with the through hole, the movement mechanism is then controlled to drive the guide needle fixing means 23 to move along the z-axis so that the guide needle 2 is moved from the first side to the second side of the xoy plane so as to enable the end 21 of the guide needle 2 to pass through the through hole and thereby be engaged with the engagement portion 11.

Figure 8A:
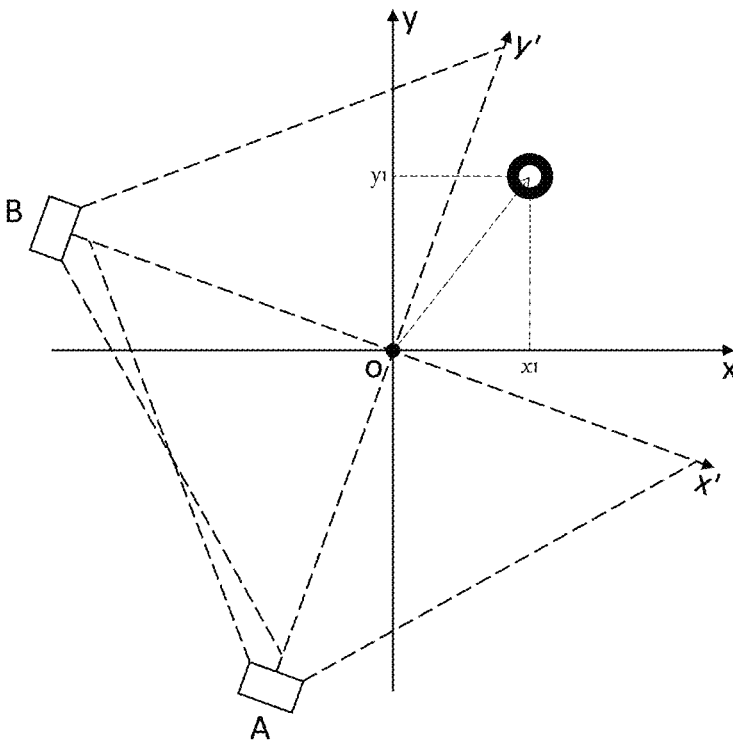
FIGS. 8A and 8B are schematic diagrams illustrating an arrangement of cameras in embodiments of the present disclosure.

In the embodiment shown in FIGS. 6B and 6C, the optical paths PA and PB of the camera A and the camera B are perpendicular to each other and perpendicular to the x-axis direction and the y-axis direction, respectively. In the embodiment shown in FIG. 8A, the optical paths PA and PB of the camera A and the camera B are perpendicular to each other, but neither of the optical paths is perpendicular to the x-axis direction or the y-axis direction. In this embodiment, the plane of view of the camera A is a plane in which ox' extends in a direction perpendicular to the paper surface, which is not parallel to the xoz plane, so that the relative position along the x-axis between the through hole of the engagement portion 11 and the end 21 cannot be directly observed by the camera A, but the projection of ox1 on ox' is observed. Accordingly, the plane of the field of view of the camera B is a plane in which oy' extends in a direction perpendicular to the paper surface, which is not parallel to the yoz plane, so that the relative position along the y-axis between the through hole of the engagement portion 11 and the end 21 cannot be directly observed by the camera B, but the projection of oy1 on oy' is observed. It will be understood by those skilled in the art that the distances x1 and y1 can be determined from the images observed by the cameras A and B by a known method such as a calibration method, and will not be described herein.

Figure 8B:
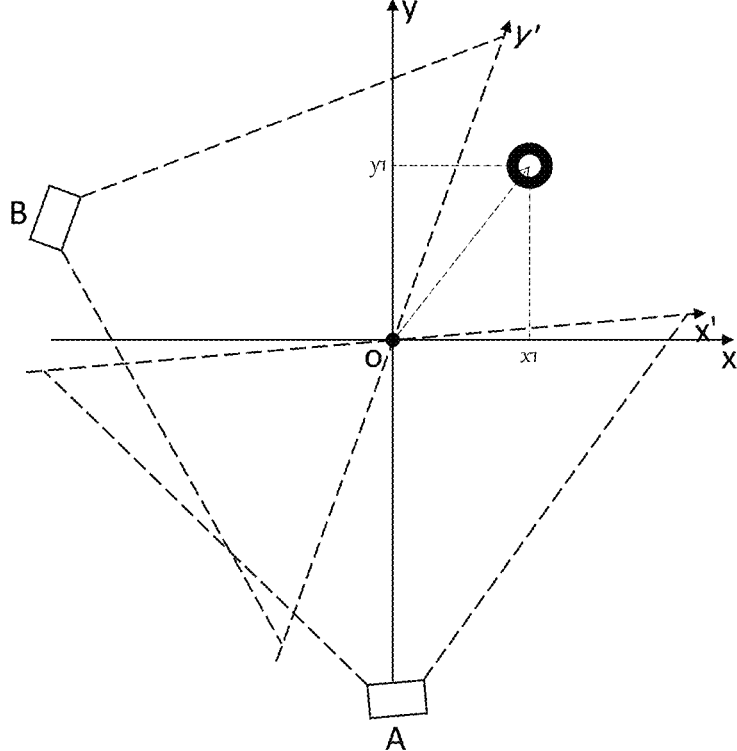

In the embodiment shown in FIGS. 6B and 6C, the optical paths PA and PB of the camera A and the camera B are perpendicular to each other. It will be understood by those skilled in the art that the optical paths PA and PB of camera A and camera B only need to be angled (i.e. non-parallel) to each other in order to achieve the object of the invention. In the embodiment shown in FIG. 8B, the optical paths PA and PB of the camera A and the camera B are not perpendicular to each other, and neither of the optical paths is perpendicular to the x-axis direction or the y-axis direction. In this embodiment, the plane of view of the camera A is a plane in which ox' extends in a direction perpendicular to the paper surface, which is not parallel to the xoz plane, so that the relative position along the x-axis between the through hole of the engagement portion 11 and the end 21 is not directly observed by the camera A, but the projection of ox1 on ox' is observed. Accordingly, the plane of the field of view of the camera B is a plane in which oy' extends in a direction perpendicular to the paper surface, which is not parallel to the yoz plane, so that the relative position along the y-axis between the through hole of the engagement portion 11 and the end 21 cannot be directly observed by the camera B, but the projection of oy1 on oy' is observed. It will be understood by those skilled in the art that the distances x1 and y1 can be determined from the images observed by the cameras A and B by a known method such as a calibration method, and will not be described herein.

Although some specific embodiments of the present disclosure have been described in detail by way of example, those skilled in the art should understand that the above examples are for illustration only and are not intended to limit the scope of the present disclosure. The various embodiments disclosed herein may be combined in any way without departing from the spirit and scope of the present disclosure. It will also be understood by those skilled in the art that various modifications can be made to the embodiments without departing from the scope and spirit of the present disclosure. The scope of the disclosure is defined by the appended claims.

The invention claimed is:

1. A system for assisting in implanting an electrode wire, comprising:

an electrode wire fixing means for fixing an electrode wire, the electrode wire being provided at an end thereof with a substantially planar metal portion having a through hole formed therein, the metal portion being at least partially suspended from the electrode wire fixing means;

a guide needle fixing means for fixing a metal guide needle, the guide needle having an end configured to mate with the through hole;

a movement mechanism configured to drive the guide needle fixing means to move such that the guide needle is moved from a first side of a plane on which the metal portion is located to a second side of the plane so as to be engaged with the metal portion, and to drive the electrode wire fixing means and/or the guide needle fixing means to move substantially parallel to the plane;

a first camera arranged on the first side of the plane and facing the metal portion, the first camera having a first optical path;

a second camera arranged on the first side of the plane and facing the metal portion, the second camera having a second optical path at an angle to the first optical path; and a processing means configured to recognize a relative position of the end of the guide needle and the through hole based on images captured by the first camera and the second camera, and control the movement mechanism to drive the electrode wire fixing means and/or the guide needle fixing means to move such that the end of the guide needle is aligned with the through hole.

2. The system according to claim 1, wherein the first camera and the second camera are arranged such that the second optical path is perpendicular to the first optical path.

3. The system according to claim 1, wherein the movement mechanism is further configured to drive the electrode wire fixing means and/or the guide needle fixing means to move substantially parallel to the plane in a first direction and a second direction perpendicular to each other, the first camera is further arranged such that the first optical path is perpendicular to the second direction, the second camera is further arranged such that the second optical path is perpendicular to the first direction.

4. The system according to claim 1, wherein the first camera and the second camera are configured to have a depth of field less than 1 millimeter.

5. The system according to claim 1, further comprising a light source configured to provide white light, or further comprising a light source configured to provide white light and a light source configured to provide blue light, or further comprising a light source configured to provide visible light, or further comprising a light source configured to provide infrared light.

6. The system according to claim 5, wherein the light source is configured such that the emitted light is irradiated after diffuse reflection onto the metal portion and/or is directly irradiated onto the metal portion.

7. The system according to claim 1, further comprising a light source configured to provide white light and a light source configured to provide blue light, wherein the light source providing white light is configured as a light source disposed coaxially with a lens of the first camera or a lens of the second camera, the light source providing blue light is configured as an annular light source sleeved outside the lens of the first camera or the lens of the second camera.

8. The system according to claim 1, wherein the first camera faces the metal portion at a first angle with respect to the plane, the second camera faces the metal portion at a second angle with respect to the plane, wherein at least one of the first angle and the second angle is less than 90 degrees.

9. The system according to claim 8, wherein at least one of the first angle and the second angle is between 20 degrees and 80 degrees.

10. The system according to claim 1, wherein the electrode wire is adhered to a substrate and the substrate is fixed to the electrode wire fixing means, the metal portion being at least partially suspended from the substrate, or wherein a plurality of electrode wires are adhered side by side to a substrate and the substrate is fixed to the electrode wire fixing means, and the processing means is further configured such that the ends of the guide needles are sequentially aligned with the through holes in the metal portions of the respective electrode wires.

11. The system according to claim 10, wherein the substrate comprises a polymer film.

12. The system according to claim 1, wherein a plurality of electrode wires are adhered side by side to a substrate and the substrate is fixed to the electrode wire fixing means, and the processing means is further configured such that the ends of the guide needles are sequentially aligned with the through holes in the metal portions of the respective electrode wires, wherein the movement mechanism is further configured to drive the electrode wire fixing means and/or the guide needle fixing means to move substantially parallel to the plane in a first direction and a second direction perpendicular to each other, the plurality of electrode wires are arranged side by side in the first direction such that the through holes in the metal portions of respective electrode wires are substantially aligned.

13. The system according to claim 12, wherein the first camera is further arranged such that the first optical path is perpendicular to the second direction, the second camera is further arranged such that the second optical path is perpendicular to the first direction.

14. The system according to claim 1, wherein the processing means is further configured to:

perform a black-and-white binarization processing on the images captured by the first camera and the second camera and perform a contour segmentation;

detect a characteristic region of the metal portion and a characteristic region of the end of the guide needle with a recognition algorithm; and compare a pixel position difference between the through hole in the metal portion and the end of the guide needle in the image, and determine a control signal for the movement mechanism according to the pixel position difference, thereby controlling the movement mechanism to drive the electrode wire fixing means and/or the guide needle fixing means to move.

15. The system according to claim 14, wherein the processing means is further configured to:

in response to the pixel position difference between the through hole in the metal portion and the end of the guide needle in the image being less than a predetermined value, control the movement mechanism to drive the guide needle fixing means to move the guide needle from the first side to the second side of the plane such that the end of the guide needle passes through the through hole and thereby is engaged with the metal portion.

16. A method for guiding an electrode wire, comprising:

performing the following operations in an environment where a predetermined brightness is reached:

viewing, by two cameras, from different angles, an engagement portion of the electrode wire for engaging a guide needle and an end of the guide needle, wherein the engagement portion of the electrode wire is provided with a through hole through which the end of the guide needle can penetrate and the electrode wire is arranged so that at least a portion of the engagement portion near the through hole is suspended, wherein both the engagement portion of the electrode wire and the end of the guide needle are configured to have a light transmittance of less than 50%; and recognizing, by a processing means, a relative position between the end of the guide needle and the through hole based on the images acquired from the two cameras and controlling the movement of the electrode wire and/or the guide needle so that the end of the guide needle is aligned with the through hole, wherein the predetermined brightness in the environment is provided by:

a light source dedicated to the environment; and/or a lighting equipment in the room in which the environment is located.

17. The method according to claim 16, wherein the light source dedicated to the environment provides white light, or wherein the light source dedicated to the environment provides white light and blue light, or wherein the light source dedicated to the environment provides visible light, or wherein the light source dedicated to the environment provides infrared light, or wherein the light emitted by the light source is irradiated after diffuse reflection onto the engagement portion of the electrode wire and/or is directly irradiated onto the engagement portion of the electrode wire.

18. The method according to claim 16, wherein the difference in light transmittance between the engagement portion of the electrode wire and the end of the guide needle is less than 15%, or wherein both the engagement portion of the electrode wire and the end of the guide needle comprise metal, or wherein both cameras have a depth of field less than 1 millimeter, or wherein the two cameras are arranged with optical paths perpendicular to each other.

19. The method according to claim 16, further comprising:

controlling movement of the electrode wire whose end is aligned with the through hole such that the end of the guide needle passes through the through hole and thereby is engaged with the engagement portion in order to guide the electrode wire.

* * * * *